(12) United States Patent
Gorczynski et al.

(10) Patent No.: US 8,206,897 B2
(45) Date of Patent: Jun. 26, 2012

(54) ASSAY FOR SOLUBLE CD200

(75) Inventors: Reginald M. Gorczynski, Willowdale (CA); Karrie Ka Wai Wong, Toronto (CA)

(73) Assignee: Trillium Therapeutics Inc., Toronto, Ontario (CA)

( * ) Notice: Subject to any disclaimer, the term of this patent is extended or adjusted under 35 U.S.C. 154(b) by 0 days.

(21) Appl. No.: 12/936,094

(22) PCT Filed: Jul. 29, 2008

(86) PCT No.: PCT/CA2008/001385
§ 371 (c)(1),
(2), (4) Date: Nov. 11, 2010

(87) PCT Pub. No.: WO2009/121162
PCT Pub. Date: Oct. 8, 2009

(65) Prior Publication Data
US 2011/0052605 A1 Mar. 3, 2011

Related U.S. Application Data

(60) Provisional application No. 61/042,342, filed on Apr. 4, 2008.

(51) Int. Cl.
*C12Q 1/00* (2006.01)
(52) U.S. Cl. .......................................................... 435/4
(58) Field of Classification Search ........................ None
See application file for complete search history.

(56) References Cited

U.S. PATENT DOCUMENTS 5,401,638 A   3/1995  Carney et al.
2005/0169870 A1 *  8/2005  Truitt et al. ................ 424/70.14

FOREIGN PATENT DOCUMENTS

WO    2007084321    7/2007

OTHER PUBLICATIONS

Huang Z., Pharmacology and Therapeutics, 2000, 86: 201-215.*
Moreaux, et al., "CD200 is a new prognostic factor in multiple myeloma", Blood, 2006, 108, pp. 4194-4197.
Brian, et al., "Co-expression of the toleragenic glycoprotein, CD200, with markers for cancer stem cells", Biochem. Biophys. Res. Commun., Dec. 2007, 364(4), pp. 778-782.
Barclay, et al., "CD200 and membrane protein interactions in the control of myeloid cells", Trends in Immunologuy, Jun. 2002, 23(6), pp. 285-290.
Brand-Rauf, Biomarkers of gene expression: Growth factors and oncoproteins, Environmental Health Perspectives, vol. 105, supplement 4, Jun. 1997, pp. 807-816.
Petermann et al., CD200 is induced by ERK and is a potential therapeutic target in melanoma, The Journal of Clinical Investigation, Dec. 2007, vol. 117, No. 12, pp. 3922-3929.
Wright et al., The usual distribution of the neuronally/lymphoid cell surface CD200 (OX2) glycoprotein is conserved in humans, Immunology, 2001, vol. 102, pp. 173-179.

* cited by examiner

*Primary Examiner* — Ilia Ouspenski
(74) *Attorney, Agent, or Firm* — Bereskin & Parr LLP; Micheline Gravelle; Carmela DeLuca

(57) ABSTRACT

The disclosure relates to methods for identifying a subject having elevated CD200 levels and/or comprising cells overexpressing CD200, the method comprising the step of assaying a biological fluid from the subject to determine a level of soluble CD200, wherein a level above control indicates the subject has elevated CD200 levels. Diagnostic methods, methods of monitoring prognosis and methods of medical treatment relating to CD200 associated medical conditions are also provided. The disclosure also provides assays and kits useful in the diagnosis of a medical condition associated with elevated CD200 and/or comprising cells overexpressing CD200.

9 Claims, 3 Drawing Sheets

ASSAY FOR SOLUBLE CD200

CROSS-REFERENCE TO RELATED APPLICATIONS

This application is a national phase application of PCT Patent Application No. CA2008/001385, filed Jul. 29, 2008, which also claims the priority benefit of U.S. Provisional Patent Application No. 61/042,342, filed Apr. 4, 2008, all of which are incorporated herein by reference in their entirety.

FIELD OF THE DISCLOSURE

The disclosure relates to the detection of a soluble form of CD200 found in biological fluids including bodily fluids as well as assays useful for diagnosing and monitoring medical conditions associated with elevated levels of CD200, such as cancer.

BACKGROUND TO THE DISCLOSURE

CD200 is a transmembrane surface protein broadly expressed on a variety of cell types and delivers immunoregulatory signals through binding to receptor (CD200R) expressed on monocytes/myeloid cells and T lymphocytes. Stimulation of CD200R triggers an immune suppression response that is of interest medically in the treatment of autoimmune disorders including rheumatoid arthritis, lupus, asthma and in graft rejection and fetal loss.

Inhibition of the CD200: CD200R cascade inhibits CD200-mediated immune suppression, and thus augments the immune response. Agents that disrupt this interaction accordingly are of interest for the treatment of infectious diseases and cancers, and particularly hematopoietic cancers including leukemia, multiple myeloma and lymphoma as well as melanoma and other cancers (Moreaux et al. Biochem. Biophys. Res. Commun., 2008, 366:117-22). It has been suggested that certain AML tumour cells display an upregulated level of membrane-bound CD200, which can be diagnostic for tumours of this type. Various groups have also reported cellular CD200 overexpression associated with CLL, multiple myeloma, and melanoma (Petermann et al, J. Clin. Invest., 2007, 117(12):3922).

As a membrane-bound protein, cellular CD200 can be detected using cell or tissue-based assays, such as flow cytometry or immunohistochemical staining methods. The use of these techniques to detect cell surface CD200 overexpression in subjects presenting with CLL has been suggested, for instance, in US2005/0129690 to Bowdish et al published Jun. 16, 2005. However, it would be desirable to provide methods that are simple in their format, to facilitate detection of CD200, particularly in subjects afflicted with tumours and other medical conditions in which CD200 is overexpressed relative to healthy subjects.

SUMMARY OF THE DISCLOSURE

It has now been found that a soluble form of CD200 is detectable in biological fluids including serum. Moreover, the level of CD200 detectable in the serum of subjects presenting with CD200-overexpressing cancers, exceeds the level of CD200 detectable in the serum of control subjects. The present disclosure therefore provides an assay useful to detect soluble CD200 in a sample extracted from a subject, wherein the assay is performed on a sample of biological fluid extracted from the subject. The disclosure further provides a method for identifying a subject having, or at risk for, a medical condition associated with increased CD200 levels and/or associated with cells and/or tumours that over-express CD200, comprising the steps of determining the level of soluble CD200 in the subject, comparing that soluble CD200 level to the soluble CD200 level in a control subject, wherein an elevated soluble CD200 level is diagnostic for a CD200 associated medical condition. The disclosure further provides for the use of the assay to monitor a subject for progression or regression of such a medical condition, such as during and after medical treatment. Also provided by the present disclosure is a method of medical treatment in which a subject is first diagnosed using the assay of the present disclosure, and is then treated, for example, treated to inhibit the CD200: CD200R signalling cascade.

Thus, in one of its aspects, the present disclosure provides a method for determining a level of soluble CD200, the method comprising contacting a biological fluid from a subject with an agent that specifically binds soluble CD200 and detecting the binding thereof to determine the level of soluble CD200.

In another aspect, the disclosure provides a method for identifying a subject having an elevated CD200 level, the method comprising the step of assaying a biological fluid from the subject to determine a level of soluble CD200, wherein a level above control indicates the subject has elevated soluble CD200 levels.

In another aspect, the disclosure provides a method for identifying a subject having cells that overexpress cellular CD200, the method comprising the step of assaying biological fluid from the subject to determine the level of soluble CD200, wherein a level above control indicates the presence of said cells.

In a related aspect, the present disclosure provides a method for identifying a subject having or at risk for a medical condition associated with elevated CD200, the method comprising the steps of:
  a) obtaining a sample of biological fluid from said subject; and
  b) determining a level of soluble CD200 in said sample, wherein a soluble CD200 level above control indicates said medical condition.

In another aspect, the present disclosure provides a method for monitoring progression in a subject of a medical condition associated with elevated CD200, the method comprising the steps of:
  a) at a first time point, determining a level of soluble CD200 in a first sample of biological fluid from the subject; and
  b) comparing the level of soluble CD200 in a subsequent sample of biological fluid taken from said subject at a second time point different from the first time point; wherein a difference in the soluble CD200 levels at the first time point compared to the second time point indicates modulated progression of the condition.

In a further aspect, the present disclosure provides a method of medical treatment useful to control progression of a medical condition associated with overexpression of cellular CD200, comprising the steps of:
  a) identifying a subject having cells that overexpress cellular CD200 as determined by the assay method of the present disclosure, and
  b) treating the subject with an agent that inhibits signalling via the CD200: CD200R pathway.

In another aspect, the disclosure provides a method of medical treatment useful to control progression of a medical condition associated with elevated levels of CD200, comprising the steps of:

a) identifying a subject having elevated levels of CD200 as determined by the assay method of the present disclosure, and b) treating the subject with an agent that inhibits signalling via the CD200: CD200R pathway.

In still a further aspect of the present disclosure, there is provided an assay useful in the diagnosis of a medical condition associated and/or mediated by cells overexpressing cellular CD200, comprising the steps of:

a) obtaining a sample of biological fluid from a subject;

b) reacting the sample with an agent that binds soluble CD200;

c) detecting bound soluble CD200; and d) comparing the level of soluble CD200 in the sample with the level of soluble CD200 in a control, wherein a subject having said medical condition is indicated by a greater level of soluble CD200 in the sample relative to the level of soluble CD200 in a control.

In yet a further aspect, there is provided an assay useful in the diagnosis of a medical condition associated with elevated levels of CD200, comprising the steps of:

a) obtaining a sample of biological fluid from a subject;

b) reacting the sample with an agent that binds soluble CD200;

c) detecting bound soluble CD200; and d) comparing the level of soluble CD200 in the sample with the level of soluble CD200 in a control, wherein a subject having said medical condition is indicated by a greater level of soluble CD200 in the sample relative to the level of soluble CD200 in a control.

A further aspect of the present disclosure relates to methods for determining prognosis in a subject with a CD200 associated disease such as cancer for example CLL comprising the steps of: assaying a biological fluid from the subject to determine a level of soluble CD200 and comparing to a reference level, wherein a level above the reference level is indicative of poor prognosis.

Also provided by the present disclosure is a kit comprising an antibody that binds soluble CD200 and instructions for the use thereof in determining the level of soluble CD200 in a sample of biological fluid.

In one embodiment, the kit comprises two antibodies, for example a capture antibody and a detector antibody. In one embodiment, the capture antibody is a rat monoclonal anti-human CD200 antibody. In another embodiment, the detector antibody is a rabbit anti-human CD200 antibody.

In embodiments of the disclosure, the sample of biological fluid is a serum sample. In other embodiments, the medical condition is cancer. In specific embodiments, the cancer is CLL, AML, MM or melanoma.

In certain embodiments, the elevated CD200 comprises elevated cellular CD200. In other embodiments, the elevated CD200 comprises elevated soluble CD200. In yet further embodiments, the elevated CD200 comprises elevated cellular and soluble CD200.

In other embodiments, the agent that inhibits signalling via the CD200: CD200R pathway is a medicament that is an antibody that binds and inhibits CD200 and/or an antibody that binds and inhibits CD200 receptor (CD200R).

In preferred embodiments, the CD200 is human CD200.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF REFERENCE TO THE FIGURES

These and other aspects of the present disclosure are now described in greater detail with reference to the accompanying drawings in which.

DETAILED DESCRIPTION OF THE DISCLOSURE

Figure 1:
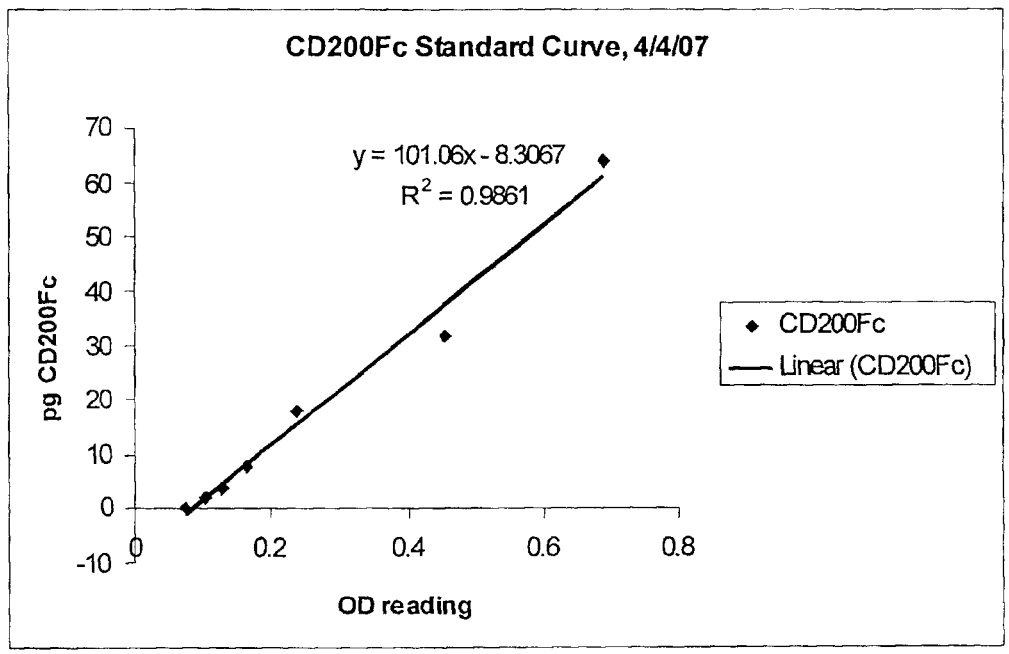
FIG. 1 is a plot of results from an assay of the present disclosure that targets the extracellular domain of CD200.

The disclosure is based on the discovery that a soluble form of CD200, i.e., a form of CD200 that is not cell membrane-bound, is detectable conveniently in biological fluid, and particularly in blood and especially serum. The disclosure therefore provides an assay useful for detecting this soluble form of CD200, i.e., "soluble CD200", in a biological fluid extracted from a subject. In aspects of the disclosure, this assay is exploited for the diagnosis and prognosis of medical conditions generally, and particularly medical conditions associated with elevated levels of CD200 and/or associated with cells, such as cancerous melanocytes, lymphocytes and leukocytes, that over-express CD200. Elevated soluble CD200 is useful particularly as a biomarker of hematopoietic cancers that are associated with elevated levels of or over-express CD200.

The methods described herein are useful for detecting increases and decreases in soluble CD200 levels.

In one aspect the disclosure provides a method for determining a level of soluble CD200, the method comprising contacting a biological fluid from a subject with an agent that specifically binds soluble CD200 and detecting the binding thereof to determine the level of soluble CD200.

The term "CD200" as used herein includes CD200 from any species or source and includes a full length CD200 polypeptide as well as fragments or portions of the polypeptide. The term "CD200" was previously referred to as "OX-2" although there has been a change in nomenclature. Both "CD200" and "OX-2" may be used interchangeably in the application. The human form of CD200 polypeptide is a polypeptide having UniProt Accession number P41217, which is an unprocessed 278-mer polypeptide that, in mature form comprises a cleaved secretion signal (residues 1-30) and an extracellular domain consisting essentially or approximately of residues 31-232. The protein may have any of the known published sequences for CD200 or OX-2. For example, CD200 sequences can be obtained from GenBank. The human sequence has accession no. M17226 X0523; the rat sequence has accession no. X01785; and the mouse sequence has accession no. AF029214.

The term "soluble CD200" or "sCD200" as used herein refers to CD200 that is not bound as a transmembrane protein to the cell membrane of a cell and that is detectable in a biological fluid. Without wishing to be bound by theory, soluble CD200 may comprise the extracellular domain of CD200 or a portion thereof that is shed or cleaved from the cell membrane. Accordingly, any portion of the extracellular domain comprised in soluble CD200 may be detected, including for example the epitope recognized by the 1B9 antibody described below.

The phrase "extracellular domain" as used herein refers to the portion of CD200 that is present on the outside surface of cells comprising for example amino acids 31 to 232 or a portion thereof such as for example amino acids 31 to 61, 62-91, 92 to 121, 122 to 151, 152-181, 182 to 211, and/or 212 to 232.

CD200 is considered to be "over-expressed", "increased", "upregulated" or "elevated" in a subject when soluble levels of CD200 in that subject exceed soluble levels of CD200 in a suitable control. A cell or tumour is said to over-express CD200 when the concentration of CD200 on the surface of that cell, or the abundance of CD200 polypeptide or message in that cell, and/or the amount released or shed exceeds the levels that are found in a control cell of that type. The presence of cell surface CD200 can be determined by staining or sorting with labelled CD200 antibody. The abundance of intracellular CD200 polypeptide can be determined by standard immunoblotting techniques and the abundance of intracellular message can be determined by standard hybridization techniques. As described herein, the abundance of CD200 released or shed from the cell surface can be determined by detecting the abundance of soluble CD200.

The term "subject" as used herein includes all members of the animal kingdom and is preferably a mammal, more preferably a human.

The term "CD200 associated medical condition" refers to any cancer associated with increased levels of CD200, including increased levels of soluble CD200 and/or cellular CD200.

In one aspect, the disclosure provides an assay for detecting CD200, which comprises the step of obtaining a sample of biological fluid from a subject, and assaying the sample to detect the presence therein of a soluble form of CD200. The soluble form of CD200 is likely derived from the form of CD200 that is cell membrane-bound, and is shed from cells that elaborate CD200 on their surface especially at levels higher than control. Soluble CD200 detectable in biological fluid can nevertheless be detected using agents that bind to the extracellular domain of cell membrane-bound CD200. To distinguish between the two forms of CD200, the present disclosures uses the term "soluble CD200" to identify the soluble, non-membrane bound form of CD200, and "cellular CD200" to identify the cell-membrane bound and/or intracellular forms of CD200.

The soluble CD200 assay of the present disclosure can be an immunoassay, or any one of the many other assay formats established for detecting a target polypeptide in a sample of biological fluid. In embodiments, the biological fluid is extracted from a human subject, and the assay accordingly is designed to detect the human form of soluble CD200. The assay can also be applied to detect other forms of CD200 native to other mammals including livestock and pets.

The phrase "biological fluid" or "sample of biological fluid" refers to any fluid sample wherein soluble CD200 may be detected, including with limitation body fluids such as blood, including whole blood or fractionated blood, including for example serum, and/or plasma. For example, the biological fluid can be fractionated by a number of methods known in the art to remove cellular components including for example red and/or white blood cells. The biological or body fluid may in the alternative be any fluid into which the soluble form of CD200 may be shed from cells that present cellular CD200, including spinal fluid, urine, bronchial alveolar lavage (BAL), saliva, ascites, semen, and the like. Also included are culture media wherein soluble CD200 may be present, for example spun culture media supernatants.

In one embodiment the sample of biological fluid is a whole blood sample. In another embodiment, the sample of biological fluid is fractionated blood including a plasma or serum fraction, and particularly serum or any serum, plasma or whole blood fraction that contains or is suspected to contain soluble CD200. In one embodiment, the biological sample comprises neat serum.

The phrase "neat serum" as used herein refers to undiluted serum.

In embodiments, the sample of biological fluid is essentially and/or substantially free from cells including cells having cellular CD200. For example, cells may be removed from a blood sample by drawing blood into evacuated tubes, allowing a clot to form, centrifuging and separating and/or transferring the resulting substantially cell free serum into a suitable container. In particular embodiments the sample of biological fluid comprises soluble factors present in the blood, as results when whole blood is filtered or fractionated to remove red blood cells. In one embodiment, the sample is substantially free of lymphocytes. In another embodiment, the sample is substantially free of myeloid lineage cells.

The term "substantially free" or "essentially free" as used herein means a sample that has no or a low level of cells by weight per fluid volume. For example, with respect to a blood sample, substantially free or essentially free means that red and white blood cells have been removed such that any remaining cells are less than about 1% of the original cell population and comprise less than about 5% and/or optionally 1% of the sample by weight per volume.

The term "control" and/or "suitable control" as used herein includes subject or subjects that are healthy and/or do not have a relevant medical condition or increased risk of a relevant medical condition, a sample obtained from, or a level derived from a subject or subjects that are healthy and/or do not have a relevant medical condition or increased risk of a relevant medical condition. For example, where the medical condition is cancer such as leukemia, the control is a sample from a subject or subjects that do not have leukemia or other condition associated with increased CD200, and/or is a value reflecting the level of CD200 in a subject or subjects that do not have leukemia or other condition associated with increased CD200. Typically the control sample corresponds to the sample type of the test subject. For example where the subject sample being assayed for CD200 is a serum sample, the control sample is typically a serum sample. A "relevant medical condition" as used herein refers to any condition associated with increased or elevated soluble CD200. As used herein a "control subject" is a subject or group of subjects that are healthy and/or do not have a relevant medical condition, a "control sample" is a sample derived from a control subject and a "control level" is a level of soluble CD200 in a control sample or control subject.

The application discloses that the level of soluble CD200 in control subjects is on average 0.427086 ng/ml ($p<0.0001$) in undiluted or neat serum and in all cases with the exception of one, less than 1 ng/ml. The average soluble CD200 level in CLL patients was 2.10323 ng/ml ($p<0.0001$) in undiluted or neat serum and was in the vast majority of cases greater than 1 ng/ml.

Accordingly, in one embodiment the control level is 0.4 ng/ml, 0.5 ng/ml, 0.6 ng/ml, 0.7 ng/ml, 0.8 ng/ml, 0.9 ng/ml, 1.0 ng/ml, 1.1 ng/ml, 1.2 ng/ml, 1.3 ng/ml, 1.4 ng/ml or 1.5 ng/ml. In one embodiment, the control level is determined in neat serum.

In another embodiment, the level of soluble CD200 in the subject tested is greater than 1.5 ng/ml, 1.6 ng/ml, 1.7 ng/ml, 1.8 ng/ml, 1.9 ng/ml or 2.0 ng/ml. In one embodiment the sample tested is neat serum.

In other embodiments, the biological fluid is concentrated. In yet other embodiments, the biological fluid is diluted. The level of soluble CD200 is in certain embodiments, determined using a standard or standard curve. A person skilled in the art will recognize that the sample is prepared (e.g. concentrated or diluted) such that the level of soluble CD200 detected falls within the linear portion of the standard curve.

The agent can be any agent that binds to soluble CD200. In certain embodiments the agent is an isolated polypeptide. In other embodiments the agent is an antibody. The agent is optionally a detection reagent that is useful for determining levels of soluble CD200 and/or a treatment reagent that is useful for treating a subject having elevated levels of CD200 and/or cells that overexpress cellular CD200.

The term "isolated polypeptide" as used herein refers to a polypeptideaceous agent, such as a peptide, polypeptide or polypeptide, which is substantially free of cellular material or culture medium when produced recombinantly, or chemical precursors, or other chemicals, when chemically synthesized.

The soluble CD200 targeted in the assay of the present disclosure is a polypeptide entity that is immunoreactive with antibodies raised against the extracellular domain of cellular CD200. Accordingly, in embodiments, the present assay exploits, as agents that target and bind soluble CD200, an antibody that binds the extracellular domain of cellular CD200. In embodiments, the antibodies are antibodies that bind the extracellular domain of human CD200. As mentioned, the human form of CD200 is a polypeptide having UniProt Accession number P41217, which is an unprocessed 278-mer polypeptide that, in mature form comprises a cleaved secretion signal (residues 1-30) and an extracellular domain consisting essentially or approximately of residues 31-232. Antibodies useful in the present assay to bind soluble CD200 accordingly are those which bind to a polypeptide having substantially (are at least 95% identical to, e.g., 96%, 97%, 98%, 99% identical to) the sequence of residues 31-232 of UniProt sequence P41217.

Antibodies that bind the extracellular domain of human and other forms of CD200 are described in the literature, and are available commercially. These commercially available antibodies include mouse anti-human CD200 monoclonal antibody from AbD Serotec and from Lifespan Biosciences, and a mouse anti-human CD200 polyclonal antibody from Abnova Corporation and Abnovus. A mouse anti-human CD200 antibody is also available from Raybiotech, packaged together with an HRP-conjugated secondary antibody, which is particularly useful in embodiments of the present disclosure.

It will be appreciated that antibodies useful in the present assay to bind soluble CD200 can, in the alternative, be produced de novo using, as antigen, intact cells presenting the membrane bound or cellular form of CD200, such as Ly5 cells exemplified herein. Alternatively, the antigen can be an isolated form of the extracellular domain of CD200 or any immunogenic fragment thereof useful to raise antibodies selective for the extracellular domain, or a fusion polypeptide comprising the extracellular domain or fragment and a carrier that enhances the immune response to the antigen, such as KLH or an Fc fusion. For vaccination, the agent can further be formulated with any adjuvant, such as Freund's, suitable for raising antibody in the selected host. The antibody production host can be any suitable mammal, such as a mouse, rat, rabbit, sheep or goat. Following immunization schedules well established in the art, the desired polyclonal antibody can be extracted from blood using the extracellular domain as affinity ligand. To form monoclonal antibodies, splenocytes from immunized animals can then be fused with a selected immortalized partner, and antibody-producing cells can be identified by selection using the CD200 extracellular domain as an affinity ligand.

More specifically, antibodies to CD200 may also be prepared using techniques known in the art such as those described by Kohler and Milstein, Nature 256, 495 (1975) and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the present disclosure, antibodies are understood to include monoclonal antibodies, polyclonal antibodies, antibody fragments (e.g., Fab, and F(ab')$_2$) and recombinantly produced binding partners.

Conventional methods can be used to prepare the antibodies. For example, by using the CD200 protein, polyclonal antisera or monoclonal antibodies can be made using standard methods. A mammal, (e.g., a mouse, hamster, or rabbit) can be immunized with an immunogenic form of the CD200 protein which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)); the EBV-hybridoma technique to produce human monoclonal antibodies (Cole et al. Monoclonal Antibodies in Cancer Therapy (1985) Allen R. Bliss, Inc., pages 77-96); and screening of combinatorial antibody libraries (Huse et al., Science 246, 1275 (1989)). Hybridoma cells can be screened immunochemically for production of antibodies specifically reactive with the CD200 protein and the monoclonal antibodies can be isolated. Therefore, the disclosure also contemplates hybridoma cells secreting monoclonal antibodies with specificity for CD200.

The term "antibody" as used herein is intended to include fragments thereof which also specifically react with CD200 or a peptide thereof. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments.

Chimeric antibody derivatives, i.e., antibody molecules that combine a non-human animal variable region and a human constant region are also contemplated within the scope of the disclosure. Chimeric antibody molecules can include, for example, the antigen binding domain from an antibody of a mouse, rat, or other species, with human constant regions. Conventional methods may be used to make chimeric antibodies containing the immunoglobulin variable region which recognizes a CD200 protein (See, for example, Morrison et al., Proc. Natl Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with the CD200 as described herein can be further humanized by producing human constant region chimeras, in which parts of the variable regions, particularly the conserved framework regions of the antigen-binding domain, are of human origin and only the hypervariable regions are of non human origin. Such immunoglobulin molecules may be made by techniques known in the art (e.g., Teng et al., Proc. Natl. Acad. Sci. U.S.A., 80, 7308-7312 (1983); Kozbor et al., Immunology Today, 4, 7279 (1983): Olsson et al., Meth. Enzymol., 92, 3-16 (1982); and PCT Publication WO 92/06193 or EP 0239400). Humanized antibodies can also be commercially produced (Scotgen Limited, 2 Holly Road, Twickenham, Middlesex, Great Britain.)

Specific antibodies, or antibody fragments reactive against CD200 may also be generated by screening expression libraries encoding immunoglobulin genes, or portions thereof, expressed in bacteria with peptides produced from nucleic acid molecules of the present disclosure. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)).

As an alternative to using antibodies that target soluble CD200, it will be appreciated that any agent having affinity and binding selectivity for soluble CD200 is useful to assay soluble CD200. In embodiments, the soluble CD200 binding agent is CD200 receptor, or any soluble CD200-binding fragment thereof. The human CD200 receptor has, substantially, the 348 amino acid sequence provided at UniProt Accession number Q6IS95. For use as an agent targeting soluble CD200, the receptor or its extracellular, CD200-binding domain can be produced as a recombinant product using established expression systems for this purpose. Production of the soluble form of the CD200 receptor as a recombinant product is described, for instance, by DeVries et al in WO2002/088164, incorporated herein by reference. Purification of the expressed product can be achieved using receptor antibody, such as the mouse anti-human CD200R MAb available from Acris Antibodies GmbH.

The present application also contemplates the use of "peptide mimetics" for detecting soluble CD200. Peptide mimetics are structures which serve as substitutes for peptides in interactions between molecules (see Morgan AND Gainor, (1989), Ann. Reports Med. Chem. 24:243-252 for a review). Peptide mimetics include synthetic structures which may or may not contain amino acids and/or peptide bonds but retain the structural and functional features of binding agents specific for polypeptide products of the biomarkers described in the present application. Peptide mimetics also include peptoids, oligopeptoids (Simon, R.J. et al. Peptoids: a modular approach to drug discovery. *Proc. Natl. Acad. Sci. U.S.A.* (1992) 89, 9367-9371).

The agent is in another embodiment an aptamer. Aptamers can be identified from a library such as a 25 mer library of $4^{25}$ random sequences of DNA molecules using the SELEX approach (Systematic Evolution of Ligands by Exponential enrichment).

The term "aptamer" as used herein means a short oligonucleotide that can bind to an antigen eg soluble CD200. The aforementioned oligonucleotide can be at least 75, 60, 50, 40, 30, 25, 20, 15 or 10 base pairs in length. The term "oligonucleotide" includes DNA and RNA, and can be double stranded or single stranded. In one embodiment, the oligonucleotide is DNA. In a further embodiment, the oligonucleotide is single stranded DNA. The term includes any oligomers or polymers of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides that contain two or more chemically distinct regions. For example, chimeric oligonucleotides may contain at least one region of modified nucleotides that confer beneficial properties (e.g. increased nuclease resistance, increased uptake into cells), or two or more oligonucleotides may be joined to form a chimeric oligonucleotide.

The aptamers of the present disclosure may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil, and 5-trifluoro cytosine.

Aptamers may contain modified phosphorous, oxygen heteroatoms in the phosphate backbone, short chain alkyl or cycloalkyl intersugar linkages or short chain heteroatomic or heterocyclic intersugar linkages. For example, the aptamers may contain phosphorothioates, phosphotriesters, methyl phosphonates, and phosphorodithioates. In an embodiment of the disclosure there are phosphorothioate bonds links between the four to six 3'-terminus bases. In another embodiment phosphorothioate bonds link all the nucleotides.

Aptamers may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P.E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an aptamer. Aptamers may also have sugar mimetics.

The aptamers may be constructed using chemical synthesis and enzymatic ligation reactions using procedures known in the art. The aptamers of the disclosure or a fragment thereof, may be chemically synthesized using naturally occurring nucleotides or variously modified nucleotides designed to increase the biological stability of the molecules or to increase the physical stability of the protein-DNA interaction (e.g. phosphorothioate derivatives and acridine substituted nucleotides). The aptamer oligonucleotide sequences may be produced biologically using an expression vector introduced into cells in the form of a recombinant plasmid, phagemid or attenuated virus in which aptamer sequences are produced under the control of a high efficiency regulatory region, the activity of which may be determined by the cell type into which the vector is introduced.

Requisite binding activity is optionally determined by identifying whether binding occurs between the aptamer and soluble CD200 by "Electrophoretic Mobility Shift Assays (EMSA)." In one embodiment, a useful oligonucleotide is identified when the oligonucleotide complexes with soluble CD200 and causes upward shift in the oligonucleotide electrophoretic mobility in a DNA retardation gel, such as a 6% polyacrylamide pre-cast DNA retardation gel. Threshold values for a selected aptamer would have its binding capacity from low picomolar affinity to and including 1 microMolar. A person skilled in the art will appreciate that other methods can be used to identify useful variants including flow cytometry, two-photon confocal microscopy, and BIAcore.

It will be appreciated that a very wide variety of assay formats can usefully be adopted for the purpose of detecting polypeptide targets, and any of these formats can be used to detect soluble CD200. In embodiments, the soluble CD200 assay is an enzyme immunoassay, such as a so-called sandwich EIA or enzyme-linked immunosorbant assay (ELISA). In its simplest form, the assay can be performed using the Western format, in which sample is dried onto a suitable substrate such as nitrocellulose, and the dried sample is then probed using a soluble CD200 binding agent that is either labelled directly or is then reacted with an secondary antibody comprising a detectable label and having binding affinity for the soluble CD200 binding agent. Washing is introduced at appropriate stages to remove background and unbound reagents. In the alternative, the assay can be performed using a capture agent bound to a solid phase, such as a soluble CD200 antibody bound to a microtitre well or conjugated to a bead such as a latex or other bead including magnetic beads or fluorescent beads. After mixing the sample and the capture agent, the bound complex is separated from the background and reacted with a detector agent that binds soluble CD200 at a site different from the capture agent. After isolating or washing the ternary complex, the presence of soluble CD200 is revealed by the presence of a label associated with the detector agent. If the label is not present on the detector agent, its presence can be established using a secondary antibody that binds the detector reagent and incorporates or is able to generate an appropriate detectable label.

It will be appreciated that a variety of labels are suitable for revealing the presence of soluble CD200 binding agent, and thereby reporting the presence of bound soluble CD200. Such labels include colloidal gold, which is useful particularly when nitrocellulose strip-based assays are used, as well as radioisotopes, fluorescent markers, luminescent markers, cytochromes, enzymes that catalyze chromogenic substrates, and the like. For example, the label may be radio-opaque or a radioisotope, such as $^3H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as biotin, alkaline phosphatase, beta-galactosidase or horseradish peroxidase; an imaging agent; or a metal ion.

In one embodiment of the disclosure, soluble CD200 is assayed by performing the steps of:
a) obtaining a sample comprising or suspected to comprise soluble CD200
b) mixing the sample with a soluble CD200-binding capture reagent that is bound to a solid phase;
c) washing the mixture;
d) mixing the washed mixture with a soluble CD200 detector reagent which binds soluble CD200 at a site different from the soluble CD200 capture reagent
e) washing the resulting mixture; and
f) determining the formation of a complex among the capture reagent, soluble CD200 and the detector reagent, the presence of the complex revealing the presence of soluble CD200 in the sample.

Thus, in embodiments, the sample is a serum sample, including a human serum sample. In other embodiments, the capture reagent is a soluble CD200 antibody. In other embodiments, the detector reagent is a soluble CD200 antibody that binds to soluble CD200 at a site different from the site bound by the capture reagent, so that both antibodies can bind soluble CD200 simultaneously. In other embodiments, the detector reagent is detectably labelled. In other embodiments the detector reagent is detected using an agent that is labelled and binds the detector reagent.

In other embodiments, the label is an enzyme, including horseradish peroxidase (HRP).

In one embodiment the assay is an immunoassay. In one embodiment the immunoassay is an ELISA (threshold of sensitivity of about 20 pg of sCD200. A person skilled in the art will recognize that the immunoassay can detect any greater amount following dilution. In another embodiment the dynamic range detected by the assay is about 50-500 pg/ml. In one embodiment the limit of detection is about 200 pg/ml.

The detection of soluble CD200 is useful particularly to identify subjects who present with medical conditions associated with elevated levels of CD200 including medical conditions associated with cells that overexpress cellular CD200. At present, it known that such conditions include various forms of hematopoietic cancers, particularly leukemias, lymphomas and multiple myeloma. In addition, melanomas particularly aggressive melanoma is associated with increased expression of cellular CD200. The cancer can be any type of cancer that expresses increased levels of CD200 including, but not limited to, hematopoietic cell cancers (including leukemias and lymphomas), colon cancer, lung cancer, kidney cancer, pancreas cancer, endometrial cancer, thyroid cancer, oral cancer, laryngeal cancer, hepatocellular cancer, bile duct cancer, squamous cell carcinoma, prostate cancer, breast cancer, cervical cancer, colorectal cancer, melanomas, and any other tumours which are antigenic or weakly antigenic. This could include, for example, EBV-induced neoplasms, and neoplasms occurring in immunosuppressed patients, e.g. transplant patients, AIDS patients, etc. and/or neoplasms associated with immunosuppression.

Without wishing to be bound by theory, soluble CD200 levels may or may not reflect membrane bound CD200 levels in a subject. For example soluble CD200 levels can be a proxy for cellular levels of CD200. However as shedding may vary, soluble CD200 may be elevated although membrane bound levels are not detectably elevated compared to control. Accordingly, detecting soluble CD200 is particularly useful as it allows increased cellular overexpression of CD200 and/or increased shedding of CD200 to be detected that is not readily detected by techniques that detect cell surface CD200.

In one embodiment the cancer is selected from renal carcinoma, head and neck carcinoma, testicular cancer, malignant mesothelioma, colon carcinoma, and MGUS/smoldering myeloma. In another embodiment the cancer is a thymoma or a myeloid tumour.

In addition, it will be appreciated that many other medical conditions may emerge as having an association with CD200 overexpression. For example, CD200 is increased in immunosuppressed subjects and/or immune deficient individuals. Transplant rejection is associated with increased immune reaction against the transplant whereas transplant survival or tolerance is associated with suppression of increased immune reaction against the transplant and increased CD200 levels. Detecting soluble CD200 levels is useful for monitoring transplant survival and/or tolerance.

Accordingly, the present disclosure provides a method useful to assess these patients generally as a population of subjects that have or are suspected of having cells that overexpress cellular CD200. The presence of such cells in these subjects can be determined initially, if desired, using immunohistochemical methods performed on tissue or cellular biopsies, or by cell sorting methods that will reveal cells having a higher than control level of CD200 on their surface. However, and in accordance with the present disclosure, the biological fluids of these subjects can, in the alternative or in combination, be assessed for soluble CD200 using the less invasive and more rapid procedure of in vitro-based diagnosis described herein.

The subjects on which the present assay method can usefully be applied thus include all of those having a medical condition for which elevated cellular CD200 is either established or suspected. In embodiments, the subjects selected for screening are those belonging to the subpopulation that presents with or is at risk for a form of cancer and particularly a hematopoietic cancer in which the tumour cells overexpress CD200. These patients in particular have been found to "shed" soluble CD200 into the bloodstream at levels diagnostic for these conditions.

Samples to be assayed for soluble CD200 include particularly samples of biological fluid extracted from patients presenting with or suspected of having hematopoietic cancers that include chronic lymphocytic leukemia (CLL) and acute myeloid leukemia (AML), and multiple myeloma (MM). Other samples to be assayed for soluble CD200 include samples of biological fluid obtained from patients presenting with or suspected of having melanoma and particularly metastatic melanoma, renal carcinoma, head and neck carcinoma, testicular cancer, malignant mesothelioma, colon carcinoma, and MGUS/smoldering myeloma. Yet other samples to be assayed for soluble CD200 are samples of biological fluid extracted from patients presenting with any other medical condition in which cells overexpress CD200, which can include patients exhibiting infection.

In embodiments, diagnosis is positive when the level of soluble CD200 is at least 2, 3 4, or five times greater in the test subject than it is in control subjects. In preferred embodiments, the level of soluble CD200 is diagnostic and/or prognostic when it is one, two, three or more log orders, or standard deviations, greater than control.

The ultimate diagnosis of the medical condition of the subject will be made when the level of soluble CD200 is assessed in combination with other factors useful to indicate the particular condition from which the subject is suffering in accordance with standard medical practise and as known to oncologists in particular.

In another aspect, the present disclosure provides a method for monitoring progression in a subject of a medical condition associated with elevated CD200, the method comprising the steps of:
a) at a first time point, determining a level of soluble CD200 in a first sample of biological fluid from the subject; and
b) comparing the level of soluble CD200 in a subsequent sample of biological fluid taken from said subject at a second time point different from the first time point;
wherein a difference in the soluble CD200 levels at the first time point compared to the second time point indicates modulated progression of the condition.

Wherein the difference is an increase in the soluble CD200 at the second time point compared to the first time point, the condition has progressed. Where there is no difference between the levels of soluble CD200 at the first and second time point, the condition has not progressed. Where the difference is a decrease in the soluble CD200 at the second time point compared to the first time point, the condition is slowing and/or resolving. In another important aspect, subjects testing positive for elevated soluble CD200 are subsequently treated, in accordance with the present disclosure, with an agent useful in the treatment of the particular condition diagnosed. In one embodiment, the subject is treated with an agent that inhibits the CD200: CD200R signalling cascade. In embodiments, the agent is an antibody that binds and inhibits CD200. In the alternative, or in combination, the agent is an antibody that binds and inhibits, i.e., is an antagonist of, the CD200 receptor. In other embodiments, the subject diagnosed by the present assay method is subsequently treated using medicines typically prescribed for use in treating the diagnosed condition. For instance, where the diagnosed condition is chronic lymphocytic leukemia (CLL), the subject can be treated chemotherapy and/or monoclonal antibody therapy, Fludarabine or cladribine is the first drug treatment for some patients. Two monoclonal antibodies, Rituxan® and Campath®, are also used to treat some CLL patients. Some other drugs used to treat CLL are chlorambucil, cyclophosphamide, doxorubicin, prednisone and vincristine. Rituxan is used with chemotherapy. Fludarabine, cyclophosphamide and Rituxan are examples of drugs that may be given together. Campath is usually used for CLL patients who have not responded to treatment with other drugs. Where the diagnosed condition is AML, the subject can be treated with chemotherapy for example, cytarabine (cytosine arainoside, ara-C) plus an anthracycline, such as idarubicin or daunorubicin. Other drugs may include high dose cytarabine, mitoxantrone and/or etoposide. Other therapies may also be used. Where the diagnosed condition is MM, the subject can be treated with chemotherapy, for example including melphalan and prednisone, stem cell transplantation, radiation therapy, plasmapheresis and immunotherapy. MM patients with refractory disease can be treated for example with bortezomib (Velcade®) in combination with doxorubicin including pegylated liposososmal doxorubicin (Doxil®).

In particular embodiments, the agent used to treat the patient diagnosed with the aid of the present assay is an agent that inhibits the CD200: CD200R interaction. Useful such agents are described in the literature and include CD200R antagonists such as CD200R antibody antagonists, soluble forms of the CD200R which interact with CD200, antibodies to CD200 which bind and inhibit its interaction with CD200R, and the like. In the case where antibodies are used as the therapeutic agent, the antibodies desirably have a human Fc region, and accordingly are either chimeric or humanized antibodies, or are human antibodies. Target-binding fragments of such antibodies are also useful as therapeutic agents.

Antibodies that bind the extracellular domain of CD200 and their use to treat cancers including hematopoietic cancers such as leukemias and lymphomas are described for instance by Gorczynski et al in U.S. Pat. No. 6,955,891 and U.S. Pat. No. 7,238,352. Other antibodies that bind CD200 and may be useful in cancer treatment are also described by Bowdish et al in WO2007/084321. These disclosures are incorporated herein by reference.

Antibodies that bind and antagonize CD200R and their use in treating cancers are described by Barclay et al, in WO00/70045, incorporated herein by reference.

Other agents that reduce CD200-mediated stimulation of CD200R include soluble forms of the CD200R as described, together with their anti-cancer use, by De Vries et al, supra, incorporated herein by reference.

In accordance with the present disclosure, the present assay is useful to monitor the progression or regression of the condition during such therapy, by assessing the relative levels of soluble CD200 in samples of biological fluid extracted from the subject at different time points during such therapy. Moreover, the present assay can reveal whether a given subject should enter such therapy, which is indicated when soluble CD200 levels exceed control. For example a decrease in the level of CD200 subsequent to therapy is indicative of positive therapeutic response and/or treatment efficacy. An increase in the level of CD200 subsequent to therapy is indicative of negative therapeutic response and/or treatment failure.

The term "treatment efficacy" and/or "positive therapeutic response" means as used herein means obtaining beneficial or desired clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. For example, no change in biomarker levels can be indicative of disease stabilization and/or prevention of disease progression. "Treatment efficacy" can also mean prolonging survival as compared to expected survival if not receiving treatment.

The term "treatment failure" or "negative therapeutic response" as used here in refers to not obtaining treatment efficacy and/or a positive therapeutic response.

Figure 4:
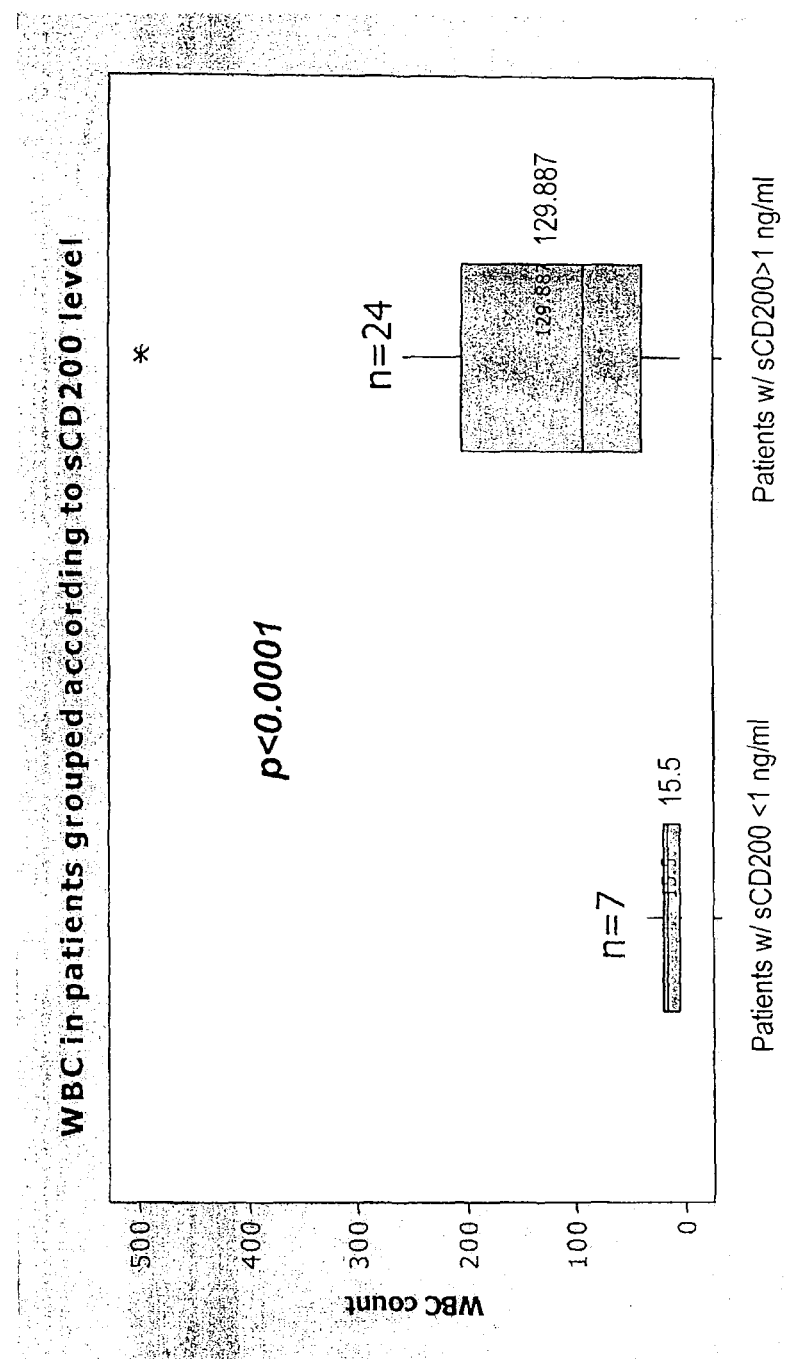
FIG. 4 is a plot showing a correlation between elevated soluble CD200 and elevated white blood cell count in CLL subjects.

Another aspect of the present disclosure relates to methods for determining prognosis in a subject with cancer, such as CLL, comprising the steps of: assaying a biological fluid from the subject to determine a level of soluble CD200 and comparing to a reference level, wherein a level above the reference level is indicative of poor prognosis. In one embodiment, the cancer is a haematological cancer. In another embodiment the cancer is CLL. In another embodiment, the cancer is AML. In yet another embodiment, the cancer is multiple myeloma. It is demonstrated herein that CLL patients with poor prognosis show significantly higher levels of soluble CD200. As shown in FIG. 4, patients with soluble CD200 levels greater than 1 ng/ml in neat serum and/or approximately 3 standard deviations higher, showed significantly higher white blood cell count (WBC), which is associated with poor prognosis in CLL subjects ($p<0.0001$). It is expected that soluble CD200 is also prognostic in other cancers such as melanoma, thymoma, renal carcinoma, head and neck carcinoma, testicular cancer, malignant mesothelioma, colon carcinoma, myeloid tumours and MGUS/smoldering myeloma. In each case, increasing levels of soluble CD200 is associated or prognostic of poor prognosis.

The term "poor prognosis" as used herein refers to prognosis associated with disease forms that are more aggressive and/or less treatable. For example, aggressive less treatable forms have poorer survival than less aggressive and/or treatable forms.

The phrase "reference level" as used herein refers to the level of soluble CD200 associated with a low WBC count, for example, an average WBC of 15.5 per 100 μl of neat serum and/or less than about 20 per 100 μl of neat serum.

In certain embodiments, the reference level is about 1 ng/ml. In other embodiments, the reference level is the average level about 1, 2, or 3 standard deviations higher than the soluble CD200 level in CLL patients with an average WBC count of 15.5, 20, 25, 30, 35, 40, 45 or 50.

The assay can be provided in kit form, comprising one or more different and separately packaged agents, including agents that bind to soluble CD200, together with instructions for the use thereof in performing the assay of the present disclosure. Optionally, the kit may further comprise a quantity of the extracellular domain of CD200, and/or a portion thereof in isolated form for use as a control or calibrator or standard in the assay. The kit may further comprise additional reagents including labelled reagents and other reactants that can be detected using instruments commonly available in the hospital or clinical laboratory.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

In the examples which follow, Example 1 describes an in vitro diagnostic assay useful to detect the extracellular domain of CD200, as a reference standard useful in the calibration and control of assays run with serum samples for the presence of soluble CD200. Example 2 describes detection of soluble CD200 in supernatant of cultured CLL Ly5 cells known to express CD200 constitutively. Example 3 describes the application of this assay for the detection of soluble CD200 in serum samples obtained from patients presenting with CLL and from healthy volunteers.

Example 1

An ELISA format was developed to detect a soluble form of CD200. For each ELISA plate (96 well, EIA/RIA, Corning), 10 ml (500 ng) of capture antibody 1B9(rat anti-human CD200 antibody, 5 ug/ml) was prepared by dilution in coating buffer (Tris-HCl, pH 8.1). To each well of the plate was added 100 ul. The prepared plates were then incubated overnight at 4C.

On the next day, the remaining solution was discarded by inverting the ELISA plate, and the plate was washed three times using 300 ul washing buffer per well (PBS+0.01% Tween 20).

An antigen standard was obtained, as an Fc fusion protein comprising the extracellular domain of CD200, and diluted to varying concentration (50 pg/ml to 500 pg/ml) using, as diluent, a blocking buffer made up of 5% FBS in PBS. To each well was added 100 ul of standard antigen. For human serum samples, 100 ul of neat serum is added per well. The plates were then incubated at room temperature for 2 hours, the wells were then aspirated, and the plates washed four times with washing buffer.

Detection antibody (rabbit anti-hCD200 serum—anti-Fc absorbed) was then prepared at 1:500 dilution using blocking buffer as diluent. One hundred microliters of detection antibody solution was then added to each well, and the plates were incubated for 2 hours at room temperature. Wells were then aspirated and the plate washed six times with wash buffer.

Secondary antibody (goat anti-rabbit IgG-HRP, Jackson) was then prepared at 1:30,000 dilution in blocking buffer, and 100 ul of secondary antibody was added to each well and then incubated at room temperature for 30 minutes. Wells were then aspirated and washed seven times with wash buffer.

To visualize the bound HRP label, 100 ul of TMB substrate was added per well. Stop solution (2M $H_2SO_4$, 50 ul) was added as soon as colour change was observed, usually within about one minute from addition of TMB, and colour change (optical density) was recorded. The results are presented in FIG. 1, providing the standard curve under these conditions.

Example 2

Figure 2:
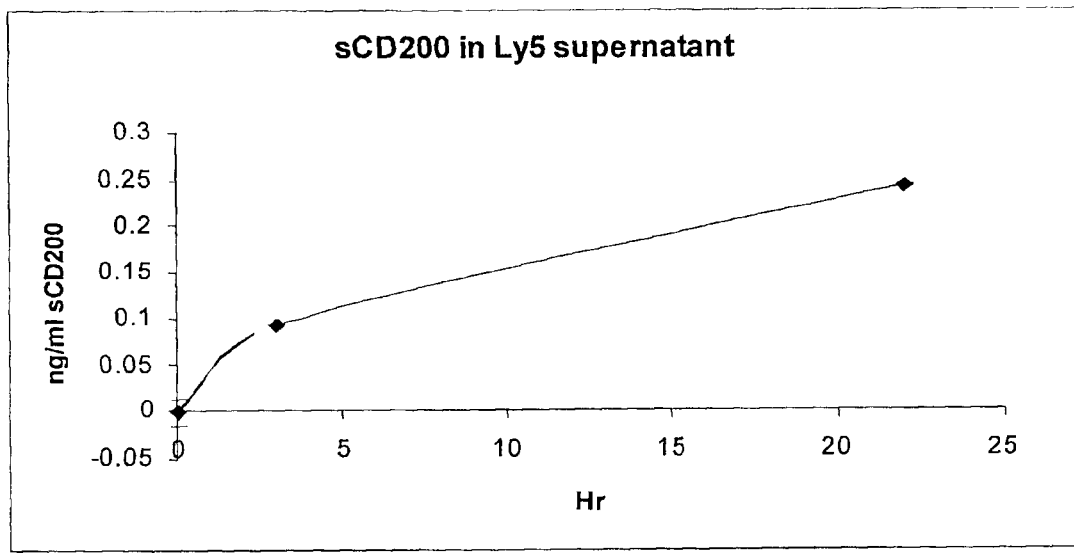
FIG. 2 is a plot of results from an assay of the supernatant of the CLL line Ly5 which constitutively expresses cellular CD200.

The assay described above was then applied in an experiment using Ly5 cells, a CLL cell line in which CD200 is expressed constitutively. Ly5 cells were cultured in serum free medium, and supernatant was assayed for the presence of soluble CD200. As shown in FIG. 2, soluble CD200 was detected in cell-free Ly5 supernatant within 3 hours after culturing. No soluble CD200 was seen when the CLL line Ly2 was similarly examined. The Ly2 line does not produce cellular CD200 at any significant level.

Example 3

The assay described above was then applied to serum samples (100 ul aliquots of neat serum) obtained from diagnosed CLL patients (n=28) ranging in age from 45-81 years with similar representation of 16 males vs. 12 females. Control samples were obtained from healthy volunteers (n=27) ranging in age from 30-50 years. All p values were obtained from the Mann Whitney test.

Figure 3:
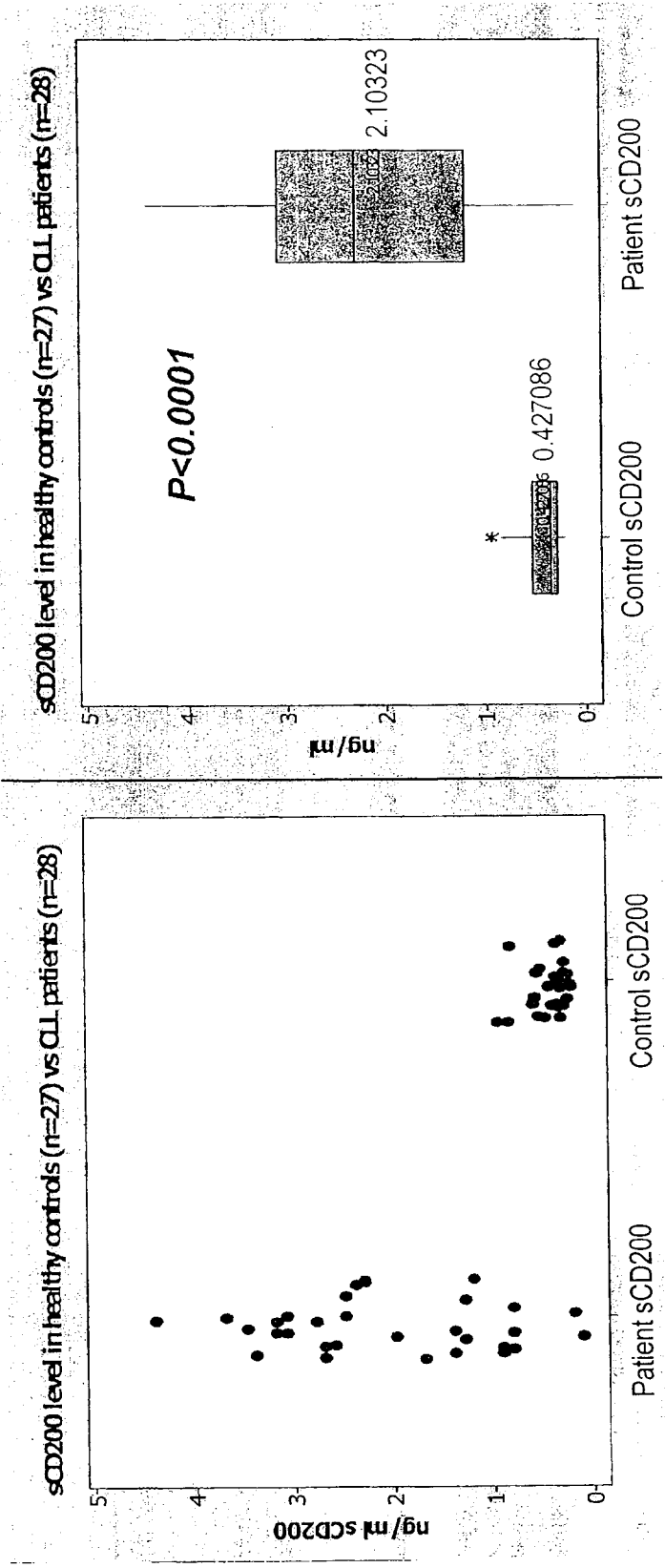
FIG. 3 is a plot showing differences in the detected levels of soluble CD200 in CLL subjects and healthy subjects.

The results are shown in FIGS. 3 and 4.

As shown in FIG. 3, panels A and B, CLL patients showed significantly higher levels of soluble CD200 compared with healthy controls. As shown in FIG. 4, CLL patients with soluble CD200 levels higher (>1 ng/ml) than 3 standard deviations from the mean of healthy controls (<1 ng/ml) showed significantly higher white blood cell count (WBC), which is associated with poor prognosis in CLL subjects.

It will thus be appreciated that a soluble form of CD200 found in serum is a biomarker useful in the diagnosis of medical conditions, such as CLL, which are associated with overexpression of CD200. Having identified CD200 in serum, the present disclosure thus provides relatively simple methods for identifying subjects in which cellular CD200 is overexpressed, thereby avoiding the need for diagnosis based on the more sophisticated techniques that target cellular-borne CD200 such as cell sorting or biopsy-based immunohistochemistry.

All publications, patents and patent applications are herein incorporated by reference in their entirety to the same extent as if each individual publication, patent or patent application was specifically and individually indicated to be incorporated by reference in its entirety.

We claim:

1. A method for identifying a subject having an elevated CD200 level, the method comprising the step of assaying body fluid from the subject to determine a level of soluble CD200, wherein a level above control indicates the subject has elevated CD200 levels.

2. The method according to claim 1 for identifying a subject having cells that overexpress CD200, wherein the CD200 is shed, released or cleaved from the cells that overexpress CD200, the method comprising the step of assaying a biological fluid from the subject to determine a level of soluble CD200, wherein a level above control indicates the presence of said cells.

3. The method according to claim 1 for identifying a subject having chronic lymphocytic leukemia (CLL), the method comprising the steps of:
   a. obtaining a sample of biological fluid from said subject; and
   b. determining a level of soluble CD200 in said sample;
   wherein a soluble CD200 level above control indicates the subject has CLL.

4. The method according to claim 1 for monitoring progression in a subject of CLL the method comprising the steps of:
   a. at a first time point, determining the level of soluble CD200 in a sample of biological fluid from the subject; and
   b. comparing the level of soluble CD200 in a sample of biological fluid taken from said subject at a second time point different from said first time point;
   wherein a difference in the soluble CD200 levels at the first time point compared to the second time point indicates modulated progression of CLL.

5. A method of medical treatment useful to control progression of CLL, comprising the steps of:
   a. identifying a subject having cells that overexpress CD200 as determined by the method according to claim 2, and
   b. treating the subject with an agent that inhibits signalling via the CD200:CD200R pathway, wherein said agent is selected from a CD200R antagonist antibody, a soluble and CD200-binding form of CD200R, and a CD200 antibody that binds soluble CD200.

6. The method according to claim 1, wherein the biological fluid comprises serum and/or plasma.

7. The method according to claim 1, wherein the biological fluid is substantially cell free.

8. An assay useful in the diagnosis of CLL, comprising the steps of:
   a. obtaining a sample of biological fluid from a subject;
   b. reacting the sample with antibody that binds soluble CD200;
   c. detecting bound soluble CD200; and
   d. comparing the level of soluble CD200 in the sample with the level of soluble CD200 in a control subject, wherein a subject having CLL is identified by a greater level of soluble CD200 in the sample relative to the level of soluble CD200 in a control subject.

9. The method according to claim 5, wherein the agent is a CD200 antibody that binds soluble CD200.

* * * * *